(12) United States Patent
Shah et al.

(10) Patent No.: US 8,348,130 B2
(45) Date of Patent: Jan. 8, 2013

(54) SURGICAL APPARATUS INCLUDING SURGICAL BUTTRESS

(75) Inventors: Sachin Shah, Milford, CT (US); Richard Simpson, Hamden, CT (US)

(73) Assignee: Covidien LP, Mansfield, MA (US)

( * ) Notice: Subject to any disclaimer, the term of this patent is extended or adjusted under 35 U.S.C. 154(b) by 6 days.

(21) Appl. No.: 12/964,916

(22) Filed: Dec. 10, 2010

(65) Prior Publication Data

US 2012/0145767 A1    Jun. 14, 2012

(51) Int. Cl.
*A61B 17/042* (2006.01)
(52) U.S. Cl. ............... 227/180.1; 227/19; 227/179.1
(58) Field of Classification Search .............. 227/19, 227/176.1, 179.1, 180.1; 606/151, 215
See application file for complete search history.

(56) References Cited

U.S. PATENT DOCUMENTS

| | | |
|---|---|---|
| 3,054,406 A | 9/1962 | Usher |
| 3,124,136 A | 3/1964 | Usher |
| 4,347,847 A | 9/1982 | Usher |
| 4,354,628 A | 10/1982 | Green |
| 4,452,245 A | 6/1984 | Usher |
| 4,605,730 A | 8/1986 | Shalaby et al. |
| 4,655,221 A | 4/1987 | Devereux |
| 4,834,090 A | 5/1989 | Moore |
| 4,838,884 A | 6/1989 | Dumican et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,205,459 A | 4/1993 | Brinkerhoff et al. |
| 5,263,629 A | 11/1993 | Trumbull et al. |
| 5,314,471 A | 5/1994 | Brauker et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk et al. |

(Continued)

FOREIGN PATENT DOCUMENTS

DE    1 99 24 311 A1    11/2000
(Continued)

OTHER PUBLICATIONS

International Search Report corresponding to European Application No. EP 10 25 0715.9, completed on Jun. 30, 2010 and mailed on Jul. 20, 2010; 3 pages.

(Continued)

*Primary Examiner* — Rinaldi Rada
*Assistant Examiner* — Nathaniel Chukwurah

(57) ABSTRACT

A surgical buttress for use with a surgical stapling apparatus having a first jaw in the form of an anvil assembly and a second jaw configured to selectively receive a staple cartridge assembly. The surgical buttress includes a first body portion and a second body portion. The first body portion substantially overlies a portion of a plurality of fastener slots of the staple cartridge assembly. The staple cartridge assembly is removably operably couplable to the second jaw of the surgical stapling apparatus. The second body portion extends from the first body portion and is configured and dimensioned to be removably positioned to substantially overlie a portion of a plurality of fastener pockets of the anvil assembly of the surgical stapling apparatus when the staple cartridge assembly is operably coupled to the second jaw of the surgical stapling apparatus.

15 Claims, 12 Drawing Sheets

U.S. PATENT DOCUMENTS

| | | | |
|---|---|---|---|
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B2 | 8/2004 | Brauker et al. |
| 6,927,315 B1 | 8/2005 | Heinecke et al. |
| 7,128,748 B2 | 10/2006 | Mooradian et al. |
| 7,147,138 B2 | 12/2006 | Shelton, IV |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,604,151 B2 | 10/2009 | Hess et al. |
| 7,665,646 B2 | 2/2010 | Prommersberger |
| 7,669,747 B2 | 3/2010 | Weisenburgh, II et al. |
| 7,744,627 B2 | 6/2010 | Orban, III et al. |
| 7,793,813 B2 | 9/2010 | Bettuchi |
| 7,823,592 B2 | 11/2010 | Bettuchi et al. |
| 7,845,533 B2 | 12/2010 | Marczyk et al. |
| 7,845,536 B2 | 12/2010 | Viola et al. |
| 7,909,224 B2 | 3/2011 | Prommersberger |
| 2002/0016626 A1 | 2/2002 | DiMatteo et al. |
| 2002/0019187 A1 | 2/2002 | Carroll et al. |
| 2002/0028243 A1 | 3/2002 | Masters |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2002/0177859 A1 | 11/2002 | Monassevitch et al. |
| 2003/0065345 A1 | 4/2003 | Weadock |
| 2003/0065346 A1 | 4/2003 | Evens et al. |
| 2003/0083676 A1 | 5/2003 | Wallace |
| 2003/0088256 A1 | 5/2003 | Conston et al. |
| 2003/0105510 A1 | 6/2003 | DiMatteo et al. |
| 2003/0114866 A1 | 6/2003 | Ulmsten et al. |
| 2003/0120284 A1 | 6/2003 | Palacios et al. |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0172048 A1 | 9/2004 | Browning |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0228446 A1 | 10/2005 | Mooradian et al. |
| 2005/0245965 A1 | 11/2005 | Orban et al. |
| 2006/0004407 A1 | 1/2006 | Hiles et al. |
| 2006/0025816 A1* | 2/2006 | Shelton ............... 606/215 |
| 2006/0085034 A1 | 4/2006 | Bettuchi |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0212050 A1 | 9/2006 | D'Agostino et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |

| | | | |
|---|---|---|---|
| 2008/0169329 A1 | 7/2008 | Shelton et al. | |
| 2008/0169330 A1 | 7/2008 | Shelton et al. | |
| 2008/0169331 A1 | 7/2008 | Shelton et al. | |
| 2008/0169332 A1 | 7/2008 | Shelton et al. | |
| 2008/0169333 A1 | 7/2008 | Shelton et al. | |
| 2008/0290134 A1 | 11/2008 | Bettuchi et al. | |
| 2008/0308608 A1 | 12/2008 | Prommersberger | |
| 2008/0314960 A1* | 12/2008 | Marczyk et al. | 227/178.1 |
| 2009/0001121 A1 | 1/2009 | Hess et al. | |
| 2009/0001122 A1 | 1/2009 | Prommersberger et al. | |
| 2009/0001123 A1 | 1/2009 | Morgan et al. | |
| 2009/0001124 A1 | 1/2009 | Hess et al. | |
| 2009/0001125 A1 | 1/2009 | Hess et al. | |
| 2009/0001126 A1 | 1/2009 | Hess et al. | |
| 2009/0001128 A1 | 1/2009 | Weisenburgh, II et al. | |
| 2009/0001130 A1 | 1/2009 | Hess et al. | |
| 2009/0005808 A1 | 1/2009 | Hess et al. | |
| 2009/0030452 A1 | 1/2009 | Bauman et al. | |
| 2009/0043334 A1 | 2/2009 | Bauman et al. | |
| 2009/0076510 A1 | 3/2009 | Bell et al. | |
| 2009/0076528 A1 | 3/2009 | Sgro | |
| 2009/0078739 A1 | 3/2009 | Viola | |
| 2009/0095791 A1 | 4/2009 | Eskaros et al. | |
| 2009/0095792 A1 | 4/2009 | Bettuchi | |
| 2009/0120994 A1 | 5/2009 | Murray et al. | |
| 2009/0134200 A1 | 5/2009 | Tarinelli et al. | |
| 2009/0206125 A1 | 8/2009 | Huitema et al. | |
| 2009/0206126 A1 | 8/2009 | Huitema et al. | |
| 2009/0206139 A1 | 8/2009 | Hall et al. | |
| 2009/0206141 A1 | 8/2009 | Huitema et al. | |
| 2009/0206142 A1 | 8/2009 | Huitema et al. | |
| 2009/0206143 A1 | 8/2009 | Huitema et al. | |
| 2009/0218384 A1 | 9/2009 | Aranyi | |
| 2009/0277947 A1 | 11/2009 | Viola | |
| 2009/0287230 A1 | 11/2009 | D'Agostino et al. | |
| 2010/0012704 A1 | 1/2010 | Tarinelli Racenet et al. | |
| 2010/0065606 A1 | 3/2010 | Stopek | |
| 2010/0065607 A1 | 3/2010 | Orban et al. | |
| 2010/0072254 A1 | 3/2010 | Aranyi et al. | |
| 2010/0147921 A1 | 6/2010 | Olson | |
| 2010/0147922 A1 | 6/2010 | Olson | |
| 2010/0147923 A1 | 6/2010 | D'Agostino et al. | |
| 2010/0243707 A1 | 9/2010 | Olson et al. | |
| 2010/0243708 A1 | 9/2010 | Aranyi et al. | |
| 2010/0243711 A1 | 9/2010 | Olson et al. | |
| 2010/0249805 A1 | 9/2010 | Olson et al. | |
| 2010/0264195 A1 | 10/2010 | Bettuchi | |
| 2010/0282815 A1 | 11/2010 | Bettuchi et al. | |
| 2011/0024476 A1 | 2/2011 | Bettuchi et al. | |
| 2011/0024481 A1 | 2/2011 | Bettuchi et al. | |
| 2011/0036894 A1 | 2/2011 | Bettuchi | |
| 2011/0042442 A1 | 2/2011 | Viola et al. | |
| 2011/0046650 A1 | 2/2011 | Bettuchi | |
| 2011/0057016 A1 | 3/2011 | Bettuchi | |

FOREIGN PATENT DOCUMENTS

| | | |
|---|---|---|
| DE | 199 24 311 A1 | 11/2000 |
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 520 525 A1 | 4/2005 |
| EP | 1 621 141 | 2/2006 |
| EP | 1 702 570 A1 | 9/2006 |
| EP | 1 759 640 A2 | 3/2007 |
| EP | 1 815 804 A2 | 8/2007 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 198 787 A1 | 6/2010 |
| EP | 2 236 098 A2 | 10/2010 |
| JP | 2000-166933 | 6/2000 |
| WO | WO 90/05489 A1 | 5/1990 |
| WO | WO 96/22055 A1 | 7/1996 |
| WO | WO 97/01989 A1 | 1/1997 |
| WO | WO 97/13463 A1 | 4/1997 |
| WO | WO 98/17180 A1 | 4/1998 |
| WO | WO 99/45849 A1 | 9/1999 |
| WO | WO 03/082126 A1 | 10/2003 |
| WO | WO 03/105698 A2 | 12/2003 |
| WO | WO 2006/023578 A2 | 3/2006 |
| WO | WO 2006/044490 A2 | 4/2006 |
| WO | WO 2006/083748 A1 | 8/2006 |
| WO | WO 2007/121579 A1 | 11/2007 |
| WO | WO 2008/057281 A2 | 5/2008 |
| WO | WO 2008/109125 A1 | 9/2008 |
| WO | WO 2010/075298 A2 | 7/2010 |
| WO | WO 2011/143183 A2 | 11/2011 |
| WO | WO 2012/044848 A1 | 4/2012 |

OTHER PUBLICATIONS

International Search Report corresponding to European Application No. EP 10 25 0642.5, completed on Mar. 25, 2011 and mailed on Apr. 4, 2011; 4 pages.

International Search Report corresponding to European Application No. EP 06 00 4598, completed on Jun. 22, 2006; 2 pages.

International Search Report corresponding to European Application No. EP 06 01 6962.0, completed on Jan. 3, 2007 and mailed on Jan. 11, 2007; 10 pages.

International Search Report corresponding to International Application No. PCT/US05/36740, completed Feb. 20, 2007 and mailed on Mar. 23, 2007; 8 pages.

International Search Report corresponding to International Application No. PCT/US2008/002981, completed Jun. 9, 2008 and mailed on Jun. 26, 2008; 2 pages.

International Search Report corresponding to European Application No. EP 08 25 1779, completed Jul. 14, 2008 and mailed on Jul. 23, 2008; 5 pages.

International Search Report corresponding to European Application No. EP 11 18 8309.6, completed on Dec. 15, 2011 and mailed on Jan. 12, 2012; 3 pages.

International Search Report corresponding to International Application No. PCT/US05/36740, completed on Feb. 20, 2007 and mailed on Mar. 23, 2007; 8 pages.

International Search Report corresponding to International Application No. PCT/US2008/002981, completed on Jun. 9, 2008 and mailed on Jun. 26, 2008; 2 pages.

International Search Report corresponding to European Application No. EP 08 25 1779, completed on Jul. 14, 2008 and mailed on Jul. 23, 2008; 5 pages.

International Search Report corresponding to European Application No. EP 08 25 1989.3, completed on Mar. 11, 2010 and mailed on Mar. 24, 2010; 3 pages.

International Search Report corresponding to European Application No. EP 05 80 4382.9, completed on Oct. 5, 2010 and mailed on Oct. 12, 2010; 3 pages.

International Search Report corresponding to European Application No. EP 10 25 1437.9, completed on Nov. 22, 2010 and mailed on Dec. 16, 2010; 3 pages.

International Search Report corresponding to European Application No. EP 09 25 2897.5, completed on Feb. 7, 2011 and mailed on Feb. 15, 2011; 3 pages.

International Search Report corresponding to European Application No. EP 12 15 2229.6, completed on Feb. 23, 2012 and mailed on Mar. 1, 2012; 4 pages.

International Search Report corresponding to European Application No. EP 12 15 0511.9, completed on Apr. 16, 2012 and mailed on Apr. 24, 2012; 7 pages.

International Search Report corresponding to European Application No. EP 12 15 2541.4, completed on Apr. 23, 2012 and mailed on May 3, 2012; 10 pages.

International Search Report corresponding to European Application No. EP 12 16 5609.4, completed on Jul. 5, 2012 and mailed on Jul. 13, 2012; 8 pages.

International Search Report corresponding to European Application No. EP 12 15 8861.0, completed on Jul. 17, 2012 and mailed on Jul. 24, 2012; 9 pages.

International Search Report corresponding to European Application No. EP 12 16 5878.5, completed on Jul. 24, 2012 and mailed on Aug. 6, 2012; 8 pages.

\* cited by examiner

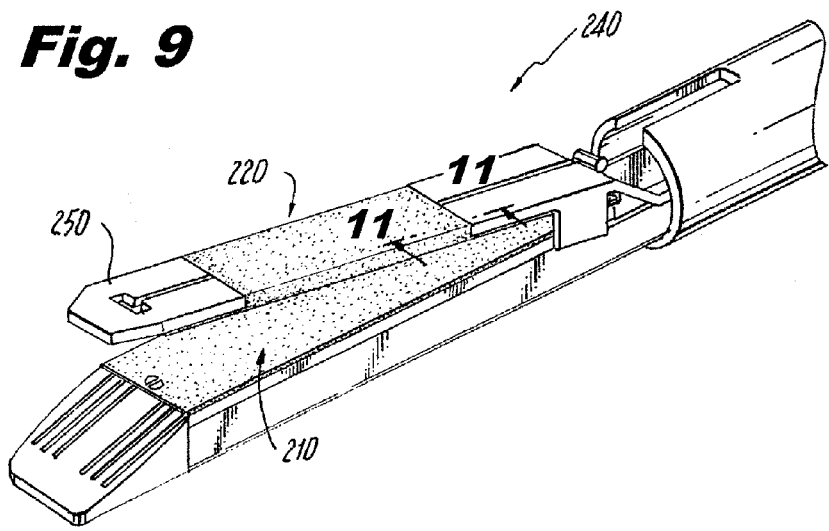
Fig. 9
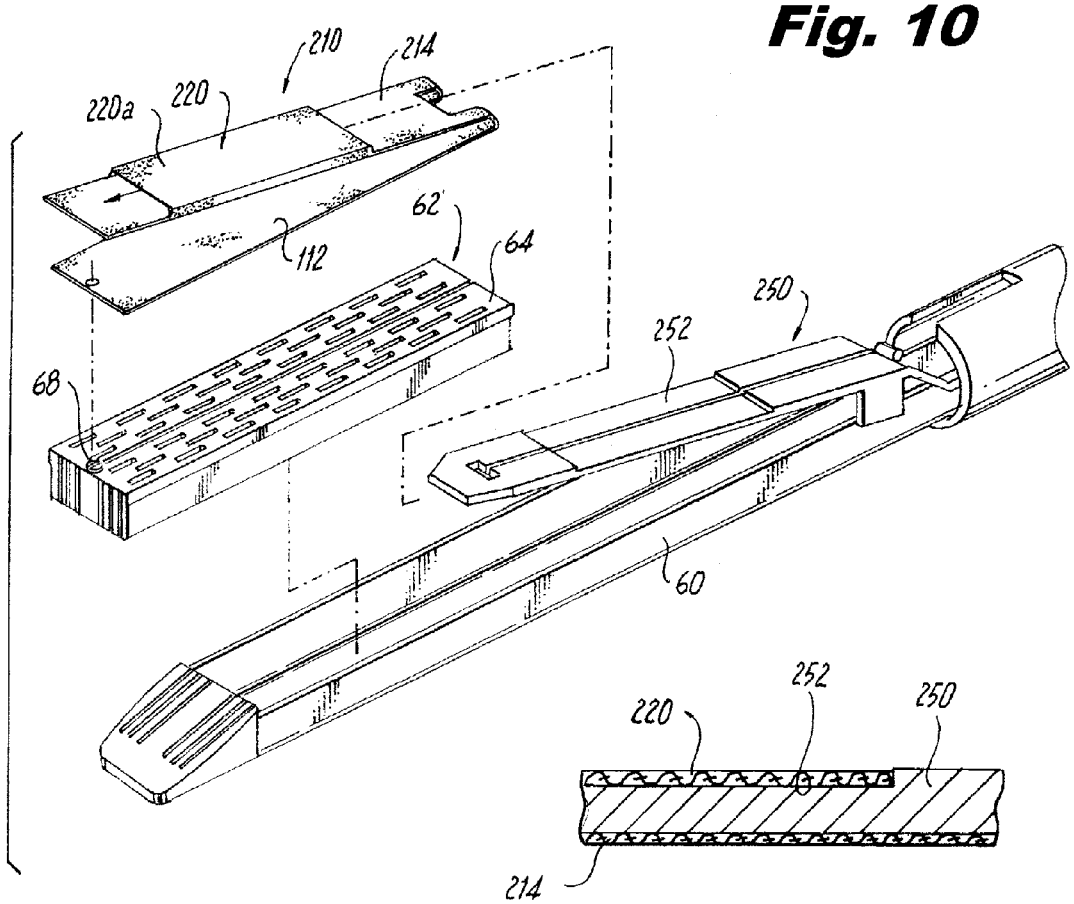
Fig. 10
Fig. 11

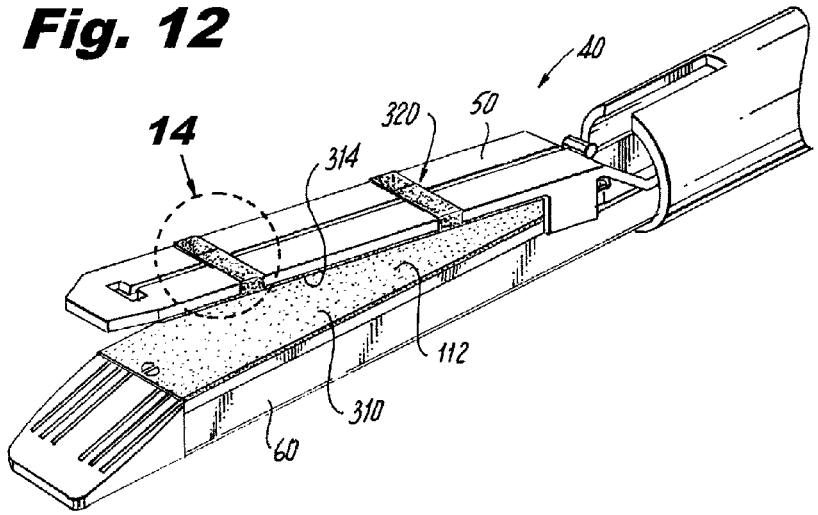
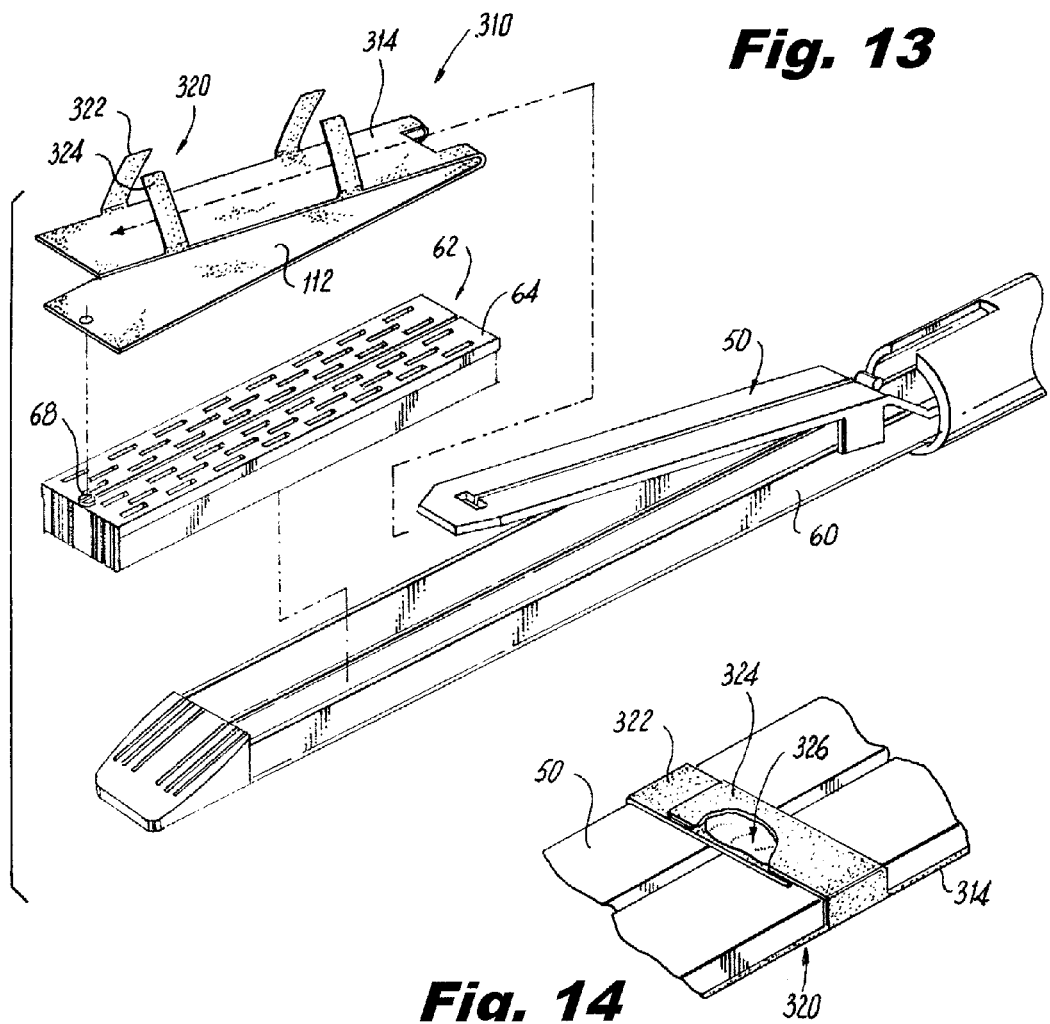

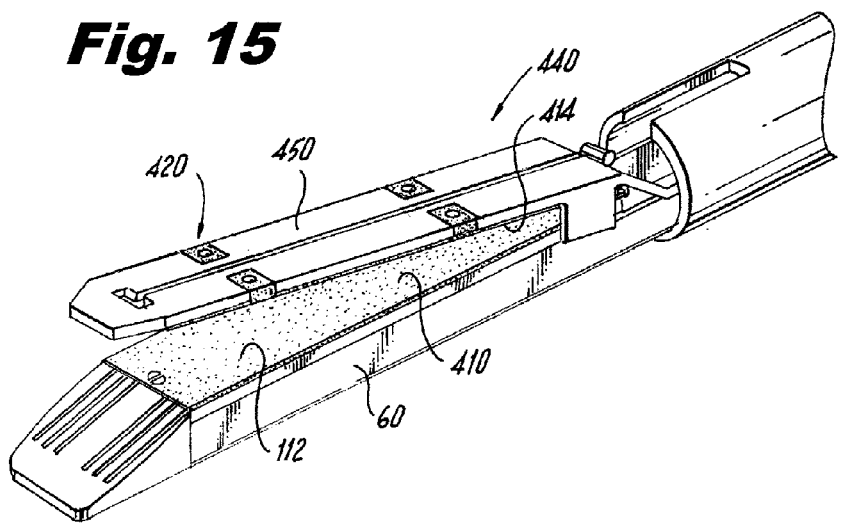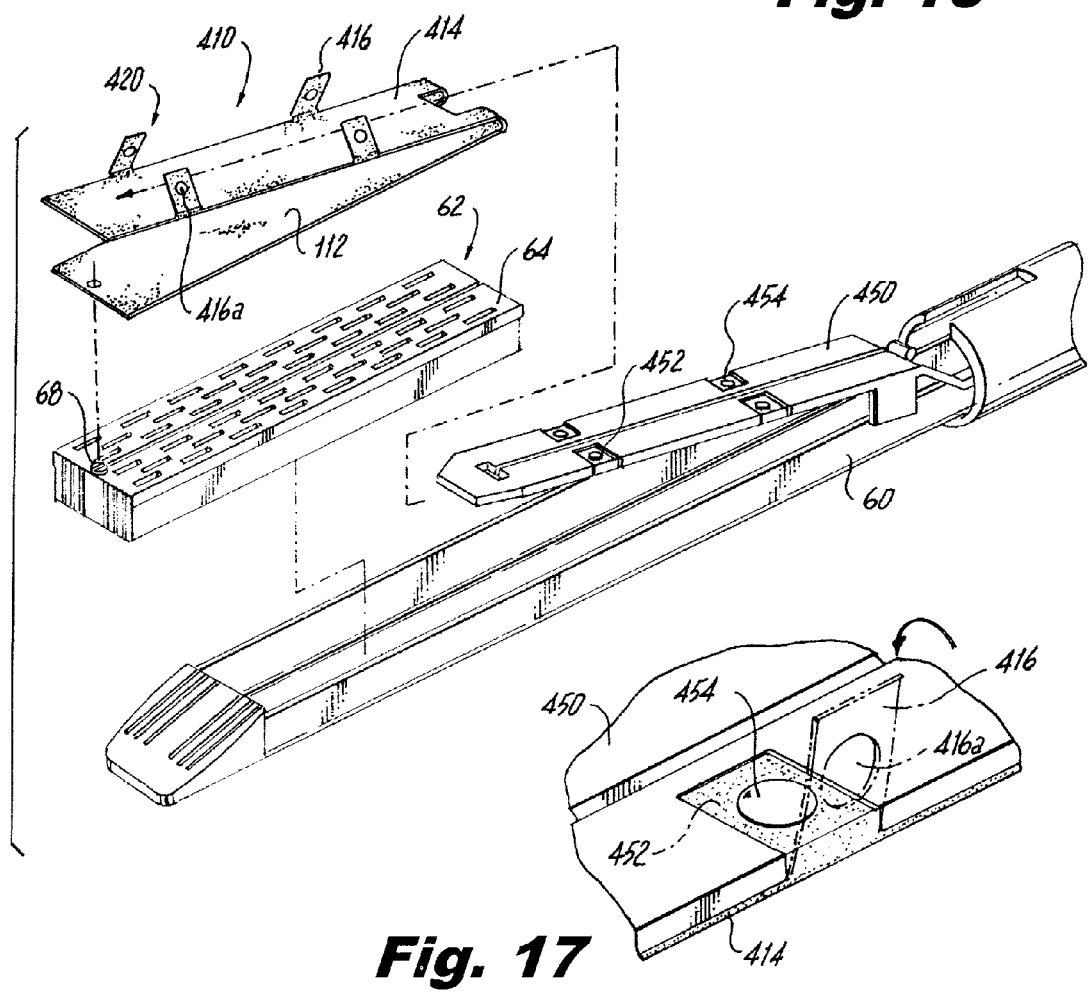

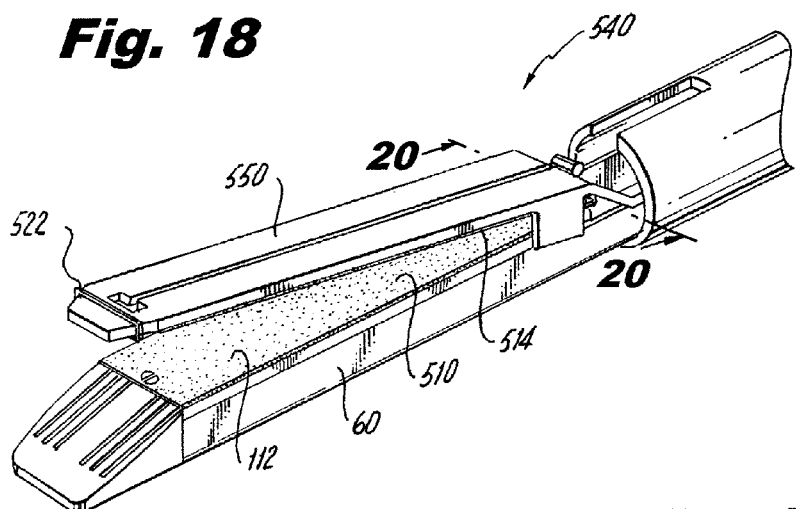
*Fig. 18*
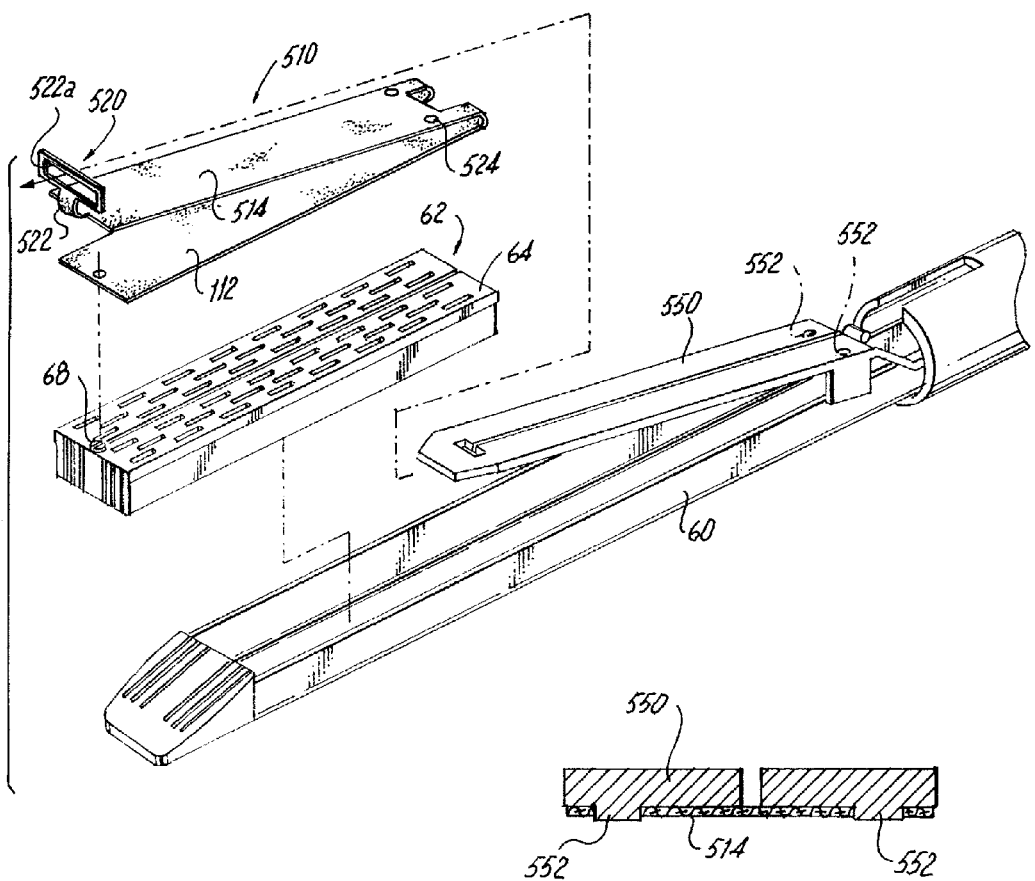
*Fig. 19*
*Fig. 20*

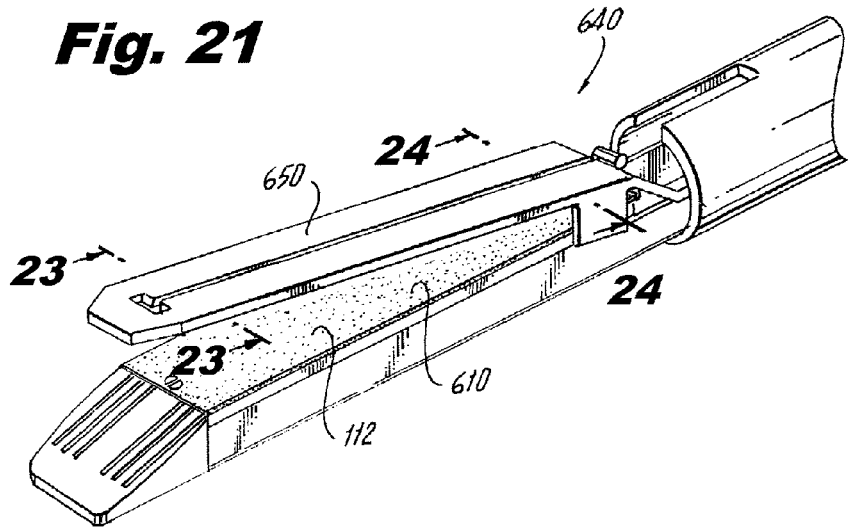
Fig. 21
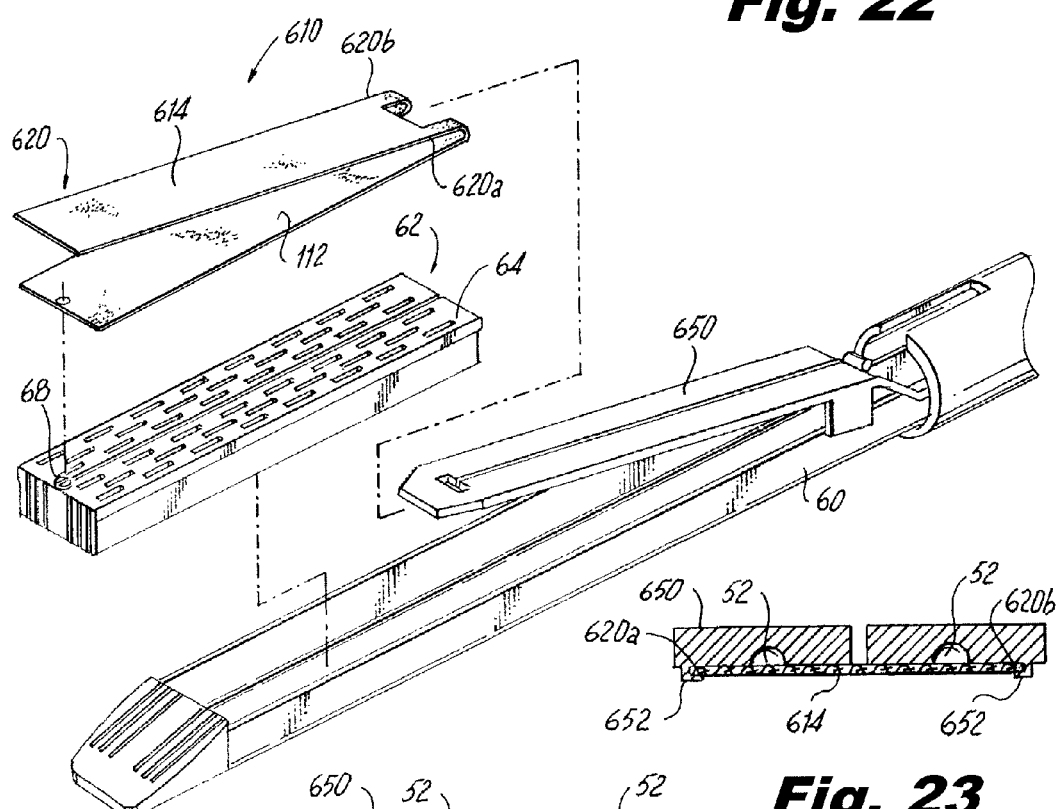
Fig. 22
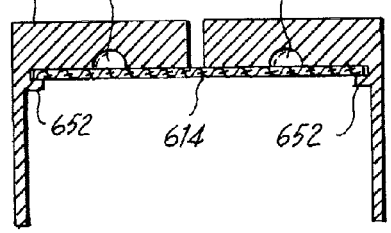
Fig. 23
Fig. 24

SURGICAL APPARATUS INCLUDING SURGICAL BUTTRESS

BACKGROUND

1. Technical Field

This application relates to a surgical apparatus, and more particularly, to a surgical buttress for use with a surgical stapling apparatus during operation of the stapling apparatus to apply a plurality of surgical staples to body tissue.

2. Background of Related Art

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and, therefore, the hospital and medical costs can be reduced as well.

Although the present disclosure includes, but is not limited to use with endoscopic surgery, endoscopic surgery is one of the truly great advances in recent years to reduce the invasiveness of surgical procedures. Generally, endoscopic surgery involves incising through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, just to name a few. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss. Heat and water loss are greatly reduced as a result of the smaller incisions. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); and U.S. Pat. No. 5,332,142 (Robinson, et al.).

In many surgical procedures, including those involved in open and endoscopic surgery, it is often necessary to staple tissue. It is especially challenging during endoscopic surgery because of the small openings through which the stapling of tissues must be accomplished. Instruments for this purpose can include two elongated members which are respectively used to capture or clamp tissue. Surgical devices wherein tissue is first grasped or clamped between opposing jaw structure and then joined by surgical fasteners are well known in the art. Typically, one of the members carries a fastener cartridge which houses a plurality of staples arranged in at least two lateral rows while the other member has an anvil that defines a surface for forming the staple legs as the staples are driven from the staple cartridge. The fasteners are typically in the form of surgical staples but two part polymeric fasteners can also be utilized. Generally, the stapling operation is effected by cam bars or wedges that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. Nos. 3,079,606 and 3,490,675.

A later stapler disclosed in U.S. Pat. No. 3,499,591 applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. U.S. Surgical, the assignee of the present application, has manufactured and marketed endoscopic stapling instruments for several years. Examples of such instruments include the Multifire ENDO GIA™ 30 and Multifire ENDO GIA™ 60 instruments. Other examples of such staplers are disclosed in U.S. Pat. Nos. 4,429,695 and 5,065,929.

In staplers of the general type described above, surgical buttress material may be used in combination with these instruments as reinforcement to staple lines to further promote proper staple formation while reducing twisting/malformation caused by any misalignment or unusual or non-uniform tissue. These instruments have provided significant clinical benefits. Nonetheless, improvements are possible, for example, by reducing the complexity of manufacture and/or application.

SUMMARY

The present invention relates to a surgical staple cartridge assembly for selective use with a surgical stapling apparatus having a first jaw in the form of an anvil assembly and a second jaw configured to selectively receive a staple cartridge assembly. The staple cartridge assembly includes a cartridge housing and a surgical buttress.

The cartridge housing defines a longitudinal axis and includes a tissue contacting surface having a plurality of rows of staple retaining slots formed therein. A staple may be disposed in each staple retaining slot.

The surgical buttress has a first body portion and a second body portion. The first body portion is secured to and overlying the tissue contacting surface of the cartridge housing. A longitudinal axis of the first body portion of the surgical buttress is substantially aligned with the longitudinal axis of the cartridge housing. The second body portion extends distally from a proximal portion of the first body portion and extends at least partially over the first body portion.

A distal end of the first body portion of the surgical buttress extends distally of a distal-most staple retaining slot of the cartridge housing. A proximal portion of the first body portion of the surgical buttress extends proximally of the staple retaining slots of the cartridge housing. The second body portion of the surgical buttress includes one or more attaching features configured to selectively attach the second body portion to the anvil assembly when the surgical staple cartridge assembly is connected to the second jaw. A proximal end of each of the first and second body portions of the surgical buttress includes a notch formed therein. Each notch is axially aligned with a knife slot of each of the cartridge housing and the anvil assembly.

The one or more attaching features may include a strap extending transversely across the second body portion. The strap is disposed on a side of the second body portion facing a tissue contacting surface of the anvil assembly when the surgical staple cartridge assembly is connected to the second jaw. In embodiments, the one or more attaching features may include a tab extending from a distal end of the second body portion. The tab may define an aperture therein that is configured and dimensioned to receive a portion of the anvil assembly.

The cartridge housing may define a knife slot. The proximal portion of the first body portion and a proximal portion of the second body portion of the surgical buttress may each include a notch formed therein, each notch being axially aligned with the knife slot.

The surgical buttress may be biodegradable or non-biodegradable.

According to one aspect, the present disclosure relates to a surgical staple cartridge for selective use in a stapling apparatus having a first jaw in the form of an anvil assembly and a second jaw configured to selectively receive the staple cartridge. The staple cartridge includes a cartridge housing, a plurality of staples, and a surgical buttress. The staple cartridge may be disposable. The plurality of staples may be disposed in staple slots formed in the cartridge housing. The one or more surgical buttresses have first and second body portions. The first body portion is mounted to the cartridge housing and the second body portion is configured and dimensioned to be removably coupled to the anvil assembly when the staple cartridge is operably coupled with the second jaw. The first body portion substantially overlies at least some of the staple slots of the cartridge housing. The second body portion is configured and dimensioned to substantially overlie at least some fastener pockets defined in the anvil assembly. The second body portion includes one or more attaching features that are configured and dimensioned to removably operably couple the second body portion to the anvil assembly. The one or more attaching features include one or more bands configured and dimensioned to extend across a back of the anvil assembly. The one or more attaching features include a tab extending from the second body portion, wherein the tab defines an aperture therein.

One or both of the first and second body portions define a passage that permits longitudinal passage of a knife of the surgical stapling apparatus therethrough. The knife extends above a tissue contacting surface of the cartridge housing.

In embodiments, at least a portion of the one or more surgical buttresses may be made from biodegradable materials selected from the group consisting of: natural collagenous materials, cat gut, and synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof. In embodiments, at least a portion of the one or more surgical buttresses may be made from non-biodegradable materials selected from the group consisting of: polyolefins, polyethylene, polydimethylsiloxane, polypropylene, copolymers of polyethylene and polypropylene, blends of polyethylene and polypropylene, ultra high molecular weight polyethylene, polyamides, polyesters, polyethylene terephthalate, polytetrafluoroethylene, polyether-esters, polybutester, polytetramethylene ether glycol, 1,4-butanediol, and polyurethanes.

According to yet another aspect, the present disclosure relates to a method of positioning a surgical buttress relative to a surgical stapling apparatus having a first jaw in the form of an anvil assembly and a second jaw configured to selectively receive a staple cartridge assembly. The method comprises the steps of: providing a disposable staple cartridge assembly including: a cartridge housing defining a longitudinal axis, the cartridge housing including a tissue contacting surface having a plurality of rows of staple retaining slots formed therein; a staple disposed in each staple retaining slot; and a surgical buttress including first and second body portions, the first body portion being secured to the staple cartridge assembly, the first body portion substantially overlying at least a portion of a plurality of fastener slots of the staple cartridge assembly, the second body portion including an attaching feature; and selectively coupling the attaching feature to the anvil assembly such that the second body portion is positioned to substantially overlie at least a portion of a plurality of fastener pockets of the anvil assembly. The method may include selectively removing at least a portion of the surgical buttress from one or both of the first jaw and the second jaw.

BRIEF DESCRIPTION OF THE DRAWINGS

The above and other aspects, features, and advantages of the present disclosure will become more apparent in light of the following detailed description when taken in conjunction with the accompanying drawings in which:

FIG. 9 is a perspective view of another embodiment of an end effector having another embodiment of a surgical buttress positioned thereon in accordance with the present disclosure;

FIG. 10 is an exploded perspective view of the end effector shown in FIG. 9;

FIG. 11 is an enlarged cross-sectional view of the indicated area of detail of FIG. 9;

FIG. 12 is a perspective view of the end effector of FIG. 2 having yet another embodiment of a surgical buttress positioned thereon in accordance with the present disclosure;

FIG. 13 is an exploded perspective view of the end effector shown in FIG. 12;

FIG. 14 is an enlarged partial perspective view of the indicated area of detail of FIG. 12;

FIG. 15 is a perspective view of still another embodiment of an end effector having still another embodiment of a surgical buttress positioned thereon in accordance with the present disclosure;

FIG. 16 is an exploded perspective view of the end effector and shown in FIG. 15;

FIG. 17 is an enlarged perspective view illustrating a portion of the surgical buttress of FIG. 15 being attached to an anvil assembly of the end effector of FIG. 15;

FIG. 18 is a perspective view of another embodiment of an end effector having another embodiment of a surgical buttress positioned thereon in accordance with the present disclosure;

FIG. 19 is an exploded perspective view of the end effector shown in FIG. 18;

FIG. 20 is a cross-sectional view of the indicated area of detail of FIG. 18;

FIG. 21 is a perspective view of yet another embodiment of an end effector having another embodiment of a surgical buttress positioned thereon in accordance with the present disclosure;

FIG. 22 is an exploded perspective view of the end effector shown in FIG. 21;

FIG. 23 is a cross-sectional view of the indicated area of detail of FIG. 21;

FIG. 24 is a cross-sectional view of the indicated area of detail of FIG. 21;

DETAILED DESCRIPTION OF EMBODIMENTS

Figure 1:
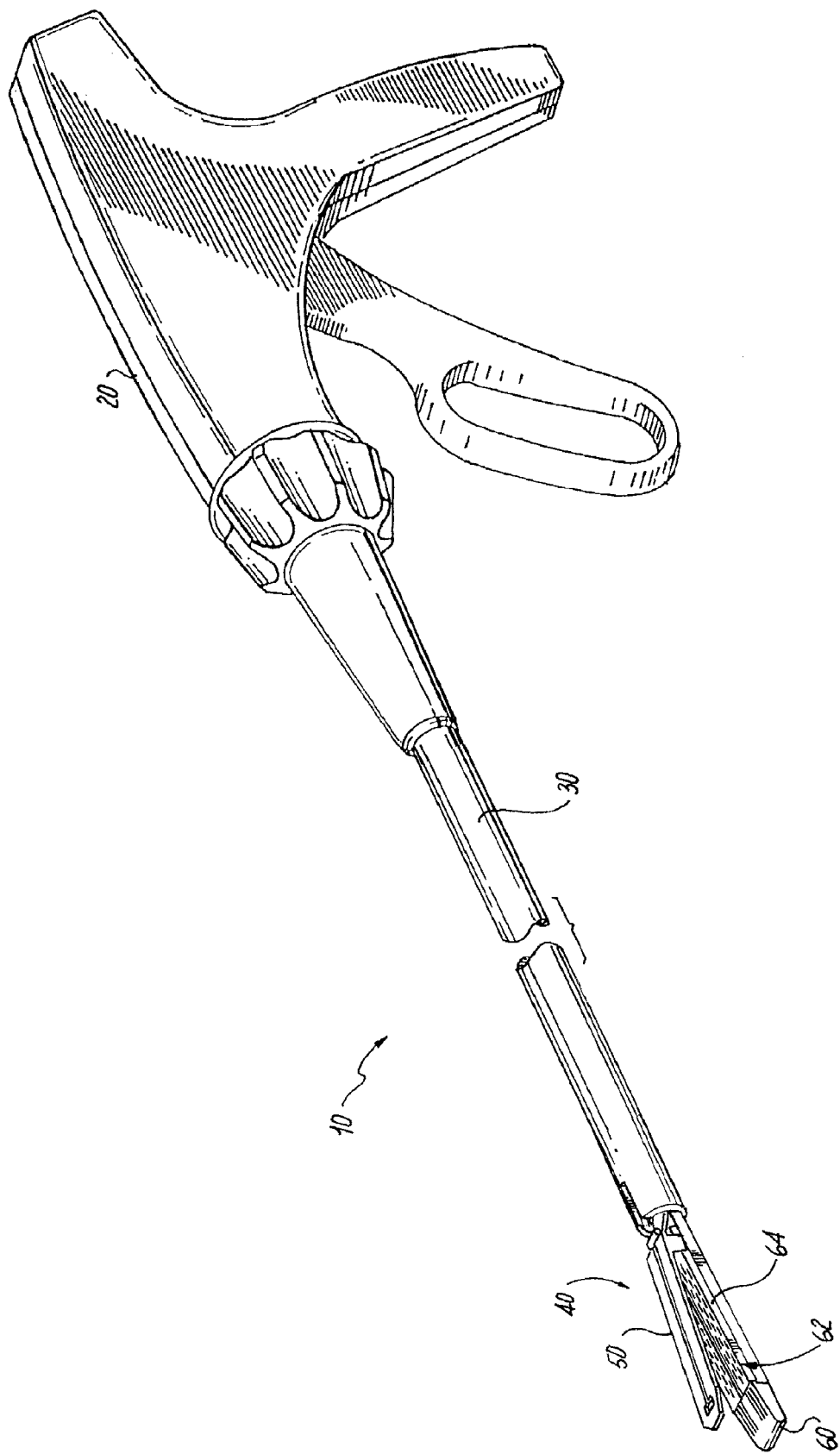
FIG. 1 is a perspective view of an exemplary endoscopic surgical stapler according to the present disclosure.

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is farther from the user. In the following description, well-known functions or constructions are not described in detail to avoid obscuring the present disclosure in unnecessary detail.

Figure 2:
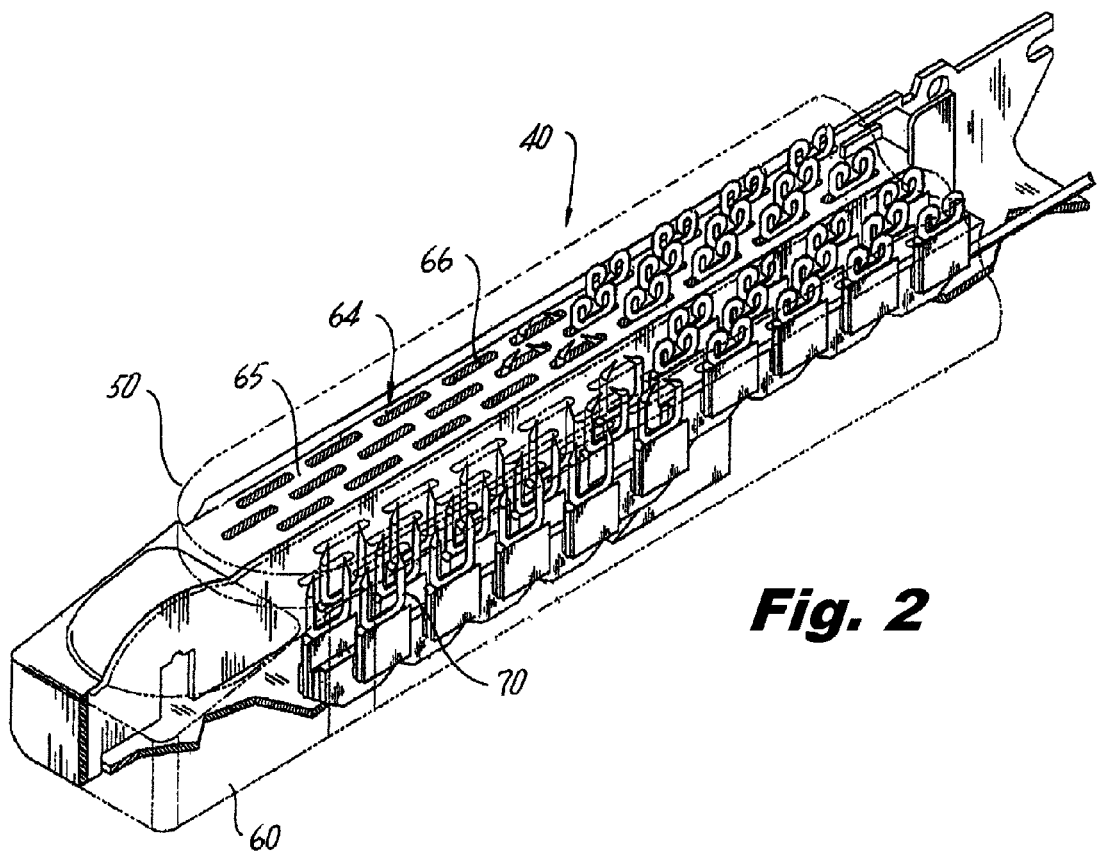
FIG. 2 is an enlarged perspective view illustrating an exemplary end effector of the surgical stapler of FIG. 1 during a fastener applying operation as fasteners are being sequentially fired.
Figure 2A:
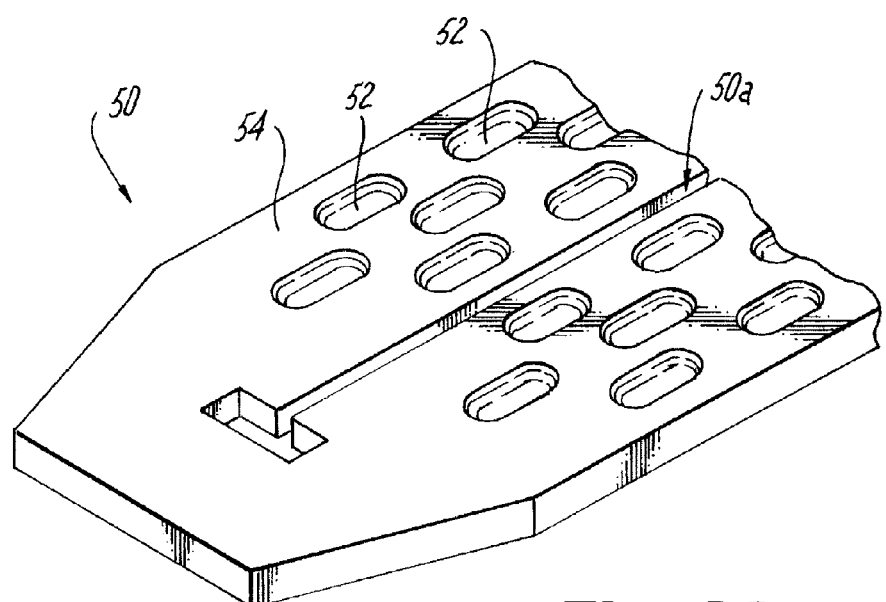
FIG. 2A is a bottom perspective view of a distal portion of an exemplary anvil of the end effector shown in FIG. 2.

Referring now to the drawings, in which like reference numerals identify identical or substantially similar parts throughout the several views, FIG. 1 illustrates a surgical stapling apparatus 10. In accordance with the present disclosure, a surgical stapling apparatus 10 includes a housing 20 and an elongate member 30 extending from the housing 20. An end effector 40 is disposed on one end of the elongate member 30. The end effector 40 includes first and second jaws 50, 60. The first jaw 50 is the form of an anvil assembly and the second jaw 60 is configured to selectively receive a staple cartridge 62. With reference to FIGS. 1 and 2, the staple cartridge 62 includes a cartridge housing 64 defining a longitudinal axis and including a tissue contact surface 65 having a plurality of rows of staple retaining slots (also referred to herein as stapler slots and fastener slots) 66 formed therein that house a plurality of fasteners or staples 70. As best shown in FIG. 2A, the plurality of staples 70 may be formed in fastener pockets 52 defined in a tissue contacting surface 54 of the first jaw 50 (anvil assembly).

Referring now to FIGS. 3-8, one embodiment of a staple cartridge assembly 100 for selective use with the surgical stapling apparatus 10 is illustrated. The staple cartridge assembly 100 includes the cartridge housing 64 and a surgical buttress 110 (as used herein, "surgical buttress" includes a pledget, gasket, buttress, or staple line reinforcement structure). In this respect, the surgical buttress 110 may be operably connected to the cartridge housing 64 via any suitable chemical or mechanical connection (e.g., adhesive, velcro, snap-fit, straps, threads, etc.). In embodiments, the cartridge housing 64 may define a catch 68 (see FIG. 4) that is positionable within an opening 111 defined within the surgical buttress 110 so that the catch 68 secures the surgical buttress 110 to the cartridge housing 64.

To perform a surgical stapling operation, the staple cartridge assembly 100 is operably coupled to the end effector 40. In particular, the staple cartridge assembly 100 is operably coupled to the second jaw 60. The staple cartridge assembly 100 may be disposable or reusable. In certain manifestations, the staple cartridge assembly 100, or portions thereof (i.e., the cartridge housing 64 and/or the surgical buttress 110), may be adapted for a single use such that the staple cartridge assembly 100 defines a single use loading unit. In this respect, upon the firing of the surgical stapling apparatus 10, the cartridge housing 64 and/or the surgical buttress 110, may be individually or collectively detachable and/or disposable.

Figure 3:
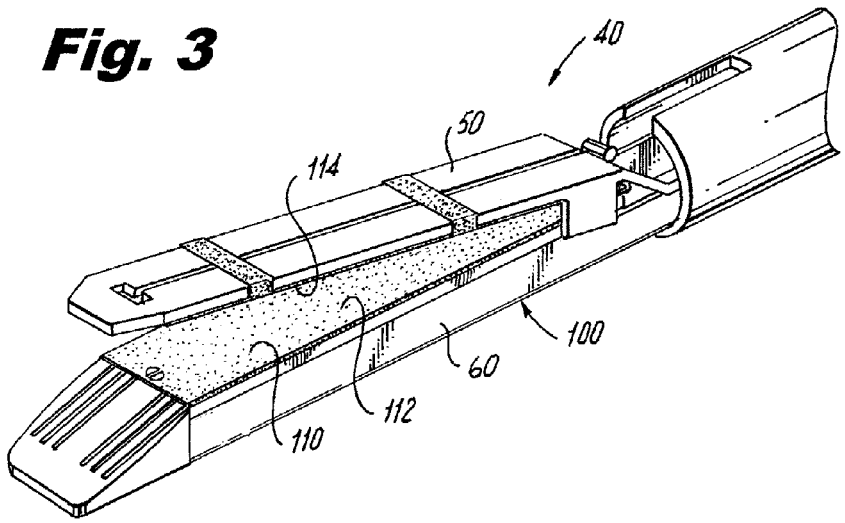
FIG. 3 is a perspective view illustrating the end effector with one embodiment of a surgical buttress, according to the present disclosure, positioned thereon.
Figure 3A:
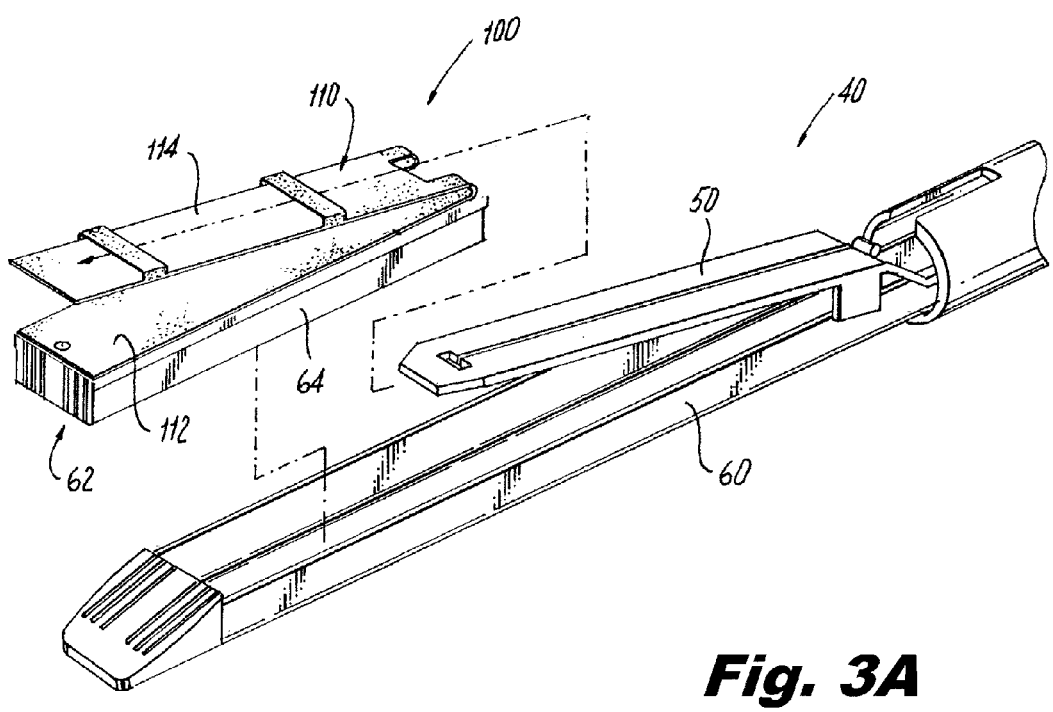
FIG. 3A is a perspective view of the end effector of FIG. 3 with a staple cartridge assembly thereof shown separated therefrom.
Figure 4:
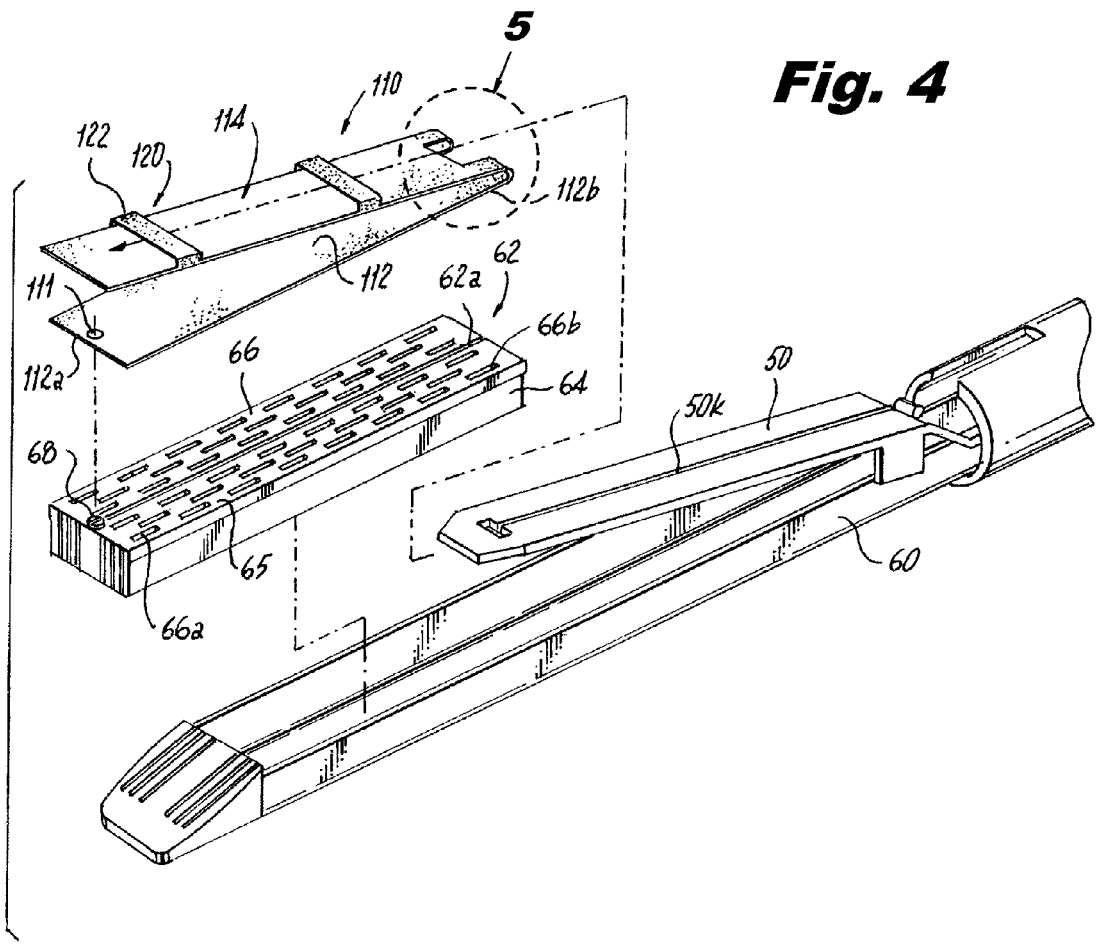
FIG. 4 is an exploded perspective view of the end effector illustrated in FIG. 3.
Figure 8:
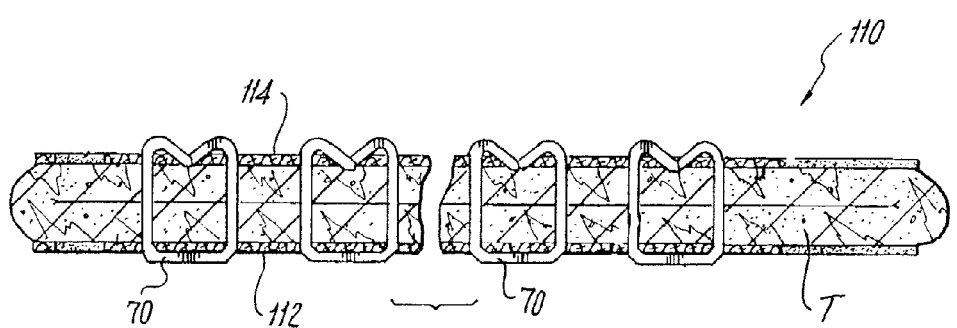
FIG. 8 is an enlarged cross-sectional view of the indicated area of detail of FIG. 7.

As best shown in FIGS. 3-4, the surgical buttress 110 has a first body portion 112 and a second body portion 114. The first body portion 112 is shown secured to and overlying the tissue contact surface 65 of the cartridge housing 64. In particular, the first body portion 112 may be secured to the tissue contact surface 65 by any suitable chemical and/or mechanical connection (e.g., adhesive, snap-fit, hook and loop type (Velcro®, Velcro Industries B.V. LTD LIAB CO NETHERLANDS) fasteners, straps, threads, etc.). For example, as mentioned above, first body portion 112 may define an opening 11 formed in a distal end thereof that is sized to receive catch 68 projecting from tissue contact surface 65 of cartridge housing 64. In this respect, the first body portion 112 may substantially overlie some or all of the fastener slots 66 of the cartridge housing 64. As such, in use, the surgical buttress 110 provides fastener-line reinforcement for the plurality of staples 70 following the firing of the surgical stapling apparatus 10 (FIG. 8). A longitudinal axis of the first body portion 112 of the surgical buttress 110 may be substantially aligned with the longitudinal axis of the cartridge housing 64.

As illustrated in FIG. 4, a distal end 112a of the first body portion 112 of the surgical buttress 110 may extend distally of a distal-most staple retaining slot 66a of the cartridge housing 64. A proximal end 112b of the first body portion 112 of the surgical buttress 110 may extend proximally of a proximal-most staple retaining slot 66b of the cartridge housing 64.

Figure 5:
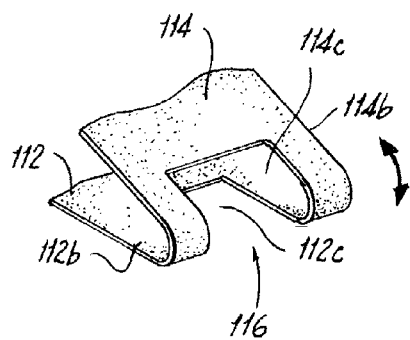
FIG. 5 is an enlarged rear perspective view of the indicated area of detail of FIG. 4.

With reference to FIGS. 4 and 5, each of the notches 112c, 114c may be axially aligned with a knife slot of each of the cartridge housing 64 and the anvil assembly 50. In particular, cartridge housing 64 defines knife slot 62a and anvil assembly 50 defines knife slot 50a. The passage 116 permits longitudinal reception of a knife (not shown) of the surgical stapling apparatus 10 therethrough to reduce any bunching of the surgical buttress 110 as the knife is distally advanced. The knife may extend above the tissue contacting surface 65 of the cartridge housing 64.

Referring again to FIG. 4, the second body portion 114 may extend from a proximal portion of the first body portion 112. Surgical buttress 110 is configured such that the second body portion 114 extends in a distal direction to extend at least partially over the first body portion 112. The second body portion 114 may substantially overlie some or all of the fastener pockets 52 (FIG. 2A) defined in the anvil assembly 50, when properly attached to anvil assembly 50, as will be described in greater detail below. The second body portion 114 of the surgical buttress 110 includes one or more attaching features 120 configured to selectively attach the second body portion 114 to the anvil assembly 50. The second body portion 114 may be removably coupled to the anvil assembly 50 when the staple cartridge 62 is operably coupled with the second jaw 60. The one or more attaching features 120 may include one or more bands or straps 122 extending transversely across the second body portion 114. Each strap 122 is disposed on a side of the second body portion 114 facing a tissue contacting surface 54 (FIG. 2A) of the anvil assembly 50 when the surgical staple cartridge assembly 100 is connected to the second jaw 60. Upon securement of the second body portion 114 to the anvil assembly 50, the straps 122 are configured and dimensioned to extend across a back of the anvil assembly 50.

As best shown in FIG. 5, a proximal portion of each of the first and second body portions 112, 114 of the surgical buttress 110 includes notches 112c, 114c, respectively, formed therein. The notches 112c, 114c collectively define a passage 116 through the surgical buttress 110.

In embodiments, at least a portion of the surgical buttress 110 may be made from biodegradable materials selected from the following group: natural collagenous materials, cat gut, and synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof. In embodiments, at least a portion of the surgical buttress 110 may be made from non-biodegradable materials selected from the following group: polyolefins, polyethylene, polydimethylsiloxane, polypropylene, copolymers of polyethylene and polypropylene, blends of polyethylene and polypropylene, ultra high molecular weight polyethylene, polyamides, polyesters, polyethylene terephthalate, polytetrafluoroethylene, polyether-esters, polybutester, polytetramethylene ether glycol, 1,4-butanediol, and polyurethanes.

Figure 6:
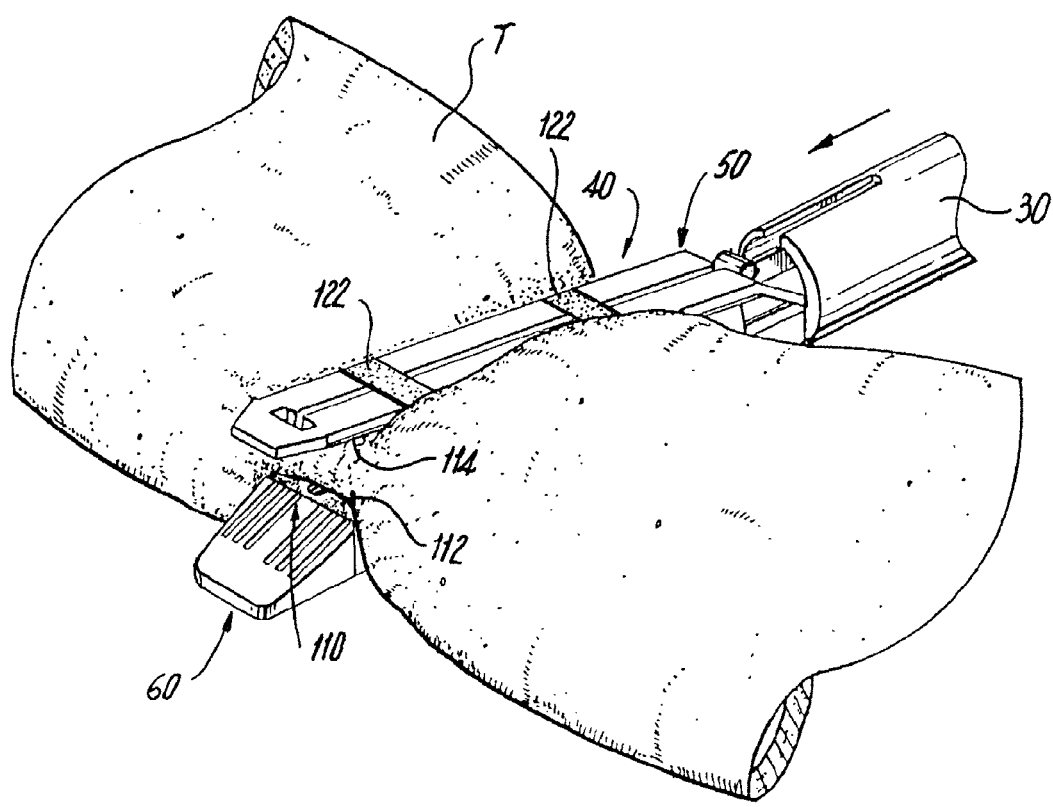
FIG. 6 is a perspective view of a distal end of the surgical stapler of FIG. 1, illustrating the jaws of the end effector of FIG. 3 being engaged with tissue.
Figure 7:
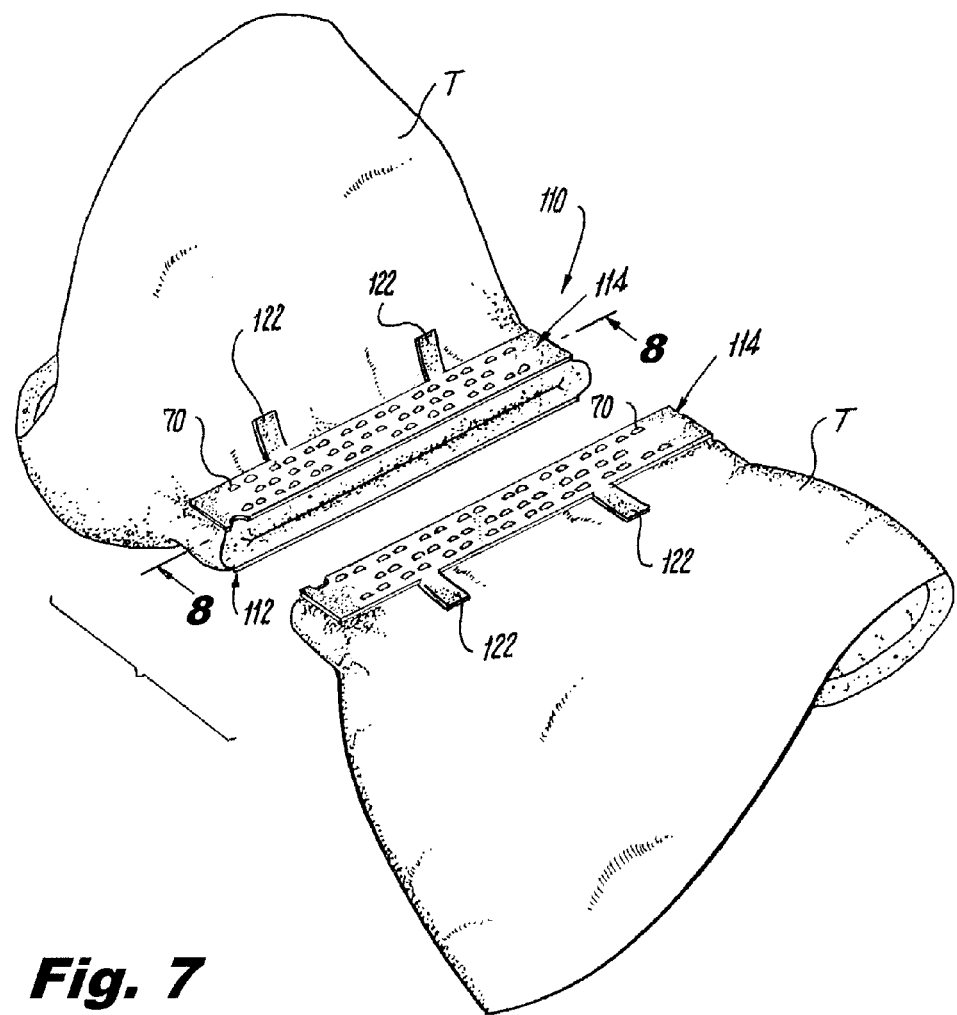
FIG. 7 is a perspective view illustrating the surgical buttress shown positioned on tissue after a fastener applying operation.

As best shown in FIG. 6, during operation of the surgical stapling apparatus 10 (FIG. 1), the first and second jaws 50, 60 are clamped against tissue "T" of a patient. As illustrated in FIGS. 2, 7, and 8, the surgical stapling apparatus 10 (FIG. 1) is fired to deploy the fasteners 70 through the fastener slots 80. Upon firing, the fasteners 70 pass through the fastener slots 66, and legs of the fasteners 70 penetrate through the tissue "T" and the body portions 112, 114 of the surgical buttress 110. The fasteners 70 are then formed against the fastener pockets 52 (FIG. 2A), thereby affixing the body portions 112, 114 of the surgical buttress 110 to the tissue "T." Concomitantly therewith, a knife (not shown) translatably disposed within the end effector 40 cuts through the tissue "T" clamped between the jaws 50, 60, through at least a portion of the body portions 112, 114 of the surgical buttress 110, and through at least a portion of one or more of the straps 122 of the surgical buttress 110. In certain embodiments, the knife can be configured and arranged to cut through the body portions 112, 114 and/or the one or more straps 122 prior to firing. As such, the one or more straps 122, which are an attaching feature 120, may be detachable to enable the surgical buttress 110 to disengage or release from the end effector 40, namely the first and second jaws 50, 60. In this manner, the surgical buttress 110 may also disengage from the cartridge housing 64 of the staple cartridge 62. Alternatively, the attaching features can be cut with shears, or can include perforations or frangible features. As seen in FIGS. 7 and 8, the central area of the body portions 112, 114 of the surgical buttress 110 remain attached to the tissue "T" via the fasteners 70.

While the staple cartridge assembly 100 is a single use loading unit, the user may remove the single use loading unit or portions thereof from the surgical stapling apparatus 10 and subsequently dispose the single use loading unit in its entirety or portions thereof. If further application is necessary, a user may replace the spent or fired single use loading unit by mounting a new single use loading unit, in the faun of a new staple cartridge assembly and a new surgical buttress 110, onto the surgical stapling apparatus 10. The user may then repeat a fastening process.

It is further contemplated that, if desired, an end user may remove surgical buttress 110 from staple cartridge assembly 100 prior to a use of surgical stapling apparatus 10.

The staple cartridge assembly, in other embodiments, houses surgical fasteners other than staples. Furthermore, the strap cartridge assembly can be arranged for use with open stapling instruments.

In further embodiments, the surgical buttress has two discrete portions attached at proximal ends of each buttress portion by adhesive, threads or bands that are separable at perforations or frangible features. Alternatively, the surgical buttress has first and second portions integral with one another.

Referring now to FIGS. 9-11, one embodiment of an end effector 240 having another embodiment of a surgical buttress 210 positioned thereon is illustrated. End effector 240 is substantially similar to end effector 40 and will be described in detail herein to the extent necessary to describe the differences in construction and operation thereof. As seen in FIGS. 9-11, end effector 240 includes an anvil assembly 250 that defines a buttress strap channel 252 therein. The buttress strap channel 252 is configured and dimensioned to receive a portion (e.g., a strap) of the surgical buttress 210 therein.

The surgical buttress 210 includes a first body portion 112, similar to surgical buttress 110, and a second body portion 214. The second body portion 214 includes an attaching feature 220. The attaching feature 220 includes a backstrap 220a that is configured and dimensioned to be positioned within the buttress strap channel 252 so that the second body portion 214 is secured to the anvil assembly 250. In this respect, the first body portion 112 is secured to the cartridge housing 64 (e.g., via catch 68, adhesive, and/or any other suitable chemical or mechanical connection) and the second body portion 214 is secured to the anvil assembly 250 when the backstrap 220a is positioned within the buttress channel 252.

In certain embodiments, a staple cartridge assembly has a cartridge body, a plurality of surgical fastener slots formed in the cartridge body, surgical fasteners disposed in the slots, and a surgical buttress. The surgical buttress is configured as a buttress material having a fold at a mid-portion thereof. The fold defines a staple cartridge portion and an anvil portion of the surgical buttress. An aperture is defined in the surgical buttress, at the fold. The staple cartridge portion is releasably attached to the cartridge body and the anvil portion has attachment features for attaching to an anvil of a surgical stapling device.

Referring now to FIGS. 12-14, another embodiment of a surgical buttress 310 is shown positioned on end effector 40. The surgical buttress 310 includes a first body portion 112, similar to surgical buttress 110, and a second body portion 314. The second body portion 314 includes at least one attaching feature 320. In particular, each attaching feature 320 includes a pair of connecting arms 322, 324 extending from opposite side edges of second body portion 314. The connecting arms 322, 324 are selectively attachable and detachable to one another via any suitable chemical or mechanical connection 326 (e.g., via adhesive, snap-fit, hook and loop type (Velcro®, Velcro Industries B.V. LTD LIAB CO NETHERLANDS) fasteners, straps or threads, etc.) so that the second body portion 314 may be secured to the anvil assembly 50. In this respect, the first body portion 112 is secured to the cartridge housing 64 (e.g., via catch 68, adhesive, or any other suitable chemical or mechanical connection) and the second body portion 314 may be selectively secured to the anvil assembly 50 via attaching feature(s) 320.

Referring now to FIGS. 15-17, one embodiment of an end effector 440 having another embodiment of a surgical buttress 410 positioned thereon or operatively associated therewith is illustrated. End effector 440 is substantially similar to end effector 40 and will be described in detail herein to the extent necessary to describe the differences in construction and operation thereof. End effector 440 includes an anvil assembly 450 that defines one or more recesses 452 formed in a back surface thereof and one or more protuberances 454 extending or projecting from the one or more recesses 452. The one or more recesses 452 and one or more protuberances 454 are configured and dimensioned to selectively couple the surgical buttress 410 to anvil assembly 450 of end effector 440.

The surgical buttress 410 includes a first body portion 112, similar to surgical buttress 110, and a second body portion 414. The second body portion 414 includes one or more attaching features 420. The one or more attaching features 420 include one or more legs 416. Each leg 416 extends from a side edge of the second body portion 414. Each leg 416 defines an aperture 416a therethrough. The aperture 416a is configured and dimensioned to be received in the one or more recesses 452 and to receive a respective one or more protuberances 454 so that the second body portion 414 is secured to the anvil assembly 450. In this respect, the first body portion 112 is secured to the cartridge housing 64 (e.g., via catch 68, adhesive, and/or any other suitable chemical or mechanical connection) and the second body portion 414 is secured to the anvil assembly 450 via the one or more attaching features 420.

Referring now to FIGS. 18-20, one embodiment of an end effector 540 having another embodiment of a surgical buttress 510 positioned thereon is illustrated. End effector 540 is substantially similar to end effector 40 and will be described in detail herein to the extent necessary to describe the differences in construction and operation thereof. End effector 540 includes an anvil assembly 550 that includes one or more extensions 552 projecting from a tissue contacting surface thereof (see FIG. 20). The one or more extensions 552 are configured and dimensioned to couple to respective openings 524 formed in the surgical buttress 510.

The surgical buttress 510 includes a first body portion 112, similar to surgical buttress 110, and a second body portion 514. The second body portion 514 includes one or more attaching features 520. The one or more attaching features 520 include a tab 522 extending from a distal end of the second body portion 514. The tab 522 defines an aperture 522a therein that is configured and dimensioned to couple to or receive the distal end of the anvil assembly 550 such that anvil assembly 550 at least partially extends through the aperture 522a. The second body portion 514 includes one or more openings 524 defined through the surgical buttress 510. The one or more openings 524 are adapted to couple to the one or more extensions 552 in order to facilitate the securement of the second body portion 514 to the anvil assembly 550. In particular, when the one or more openings 524 are positioned on the extensions 552, the surgical buttress 510 is inhibited from axially translating along the end effector 540. Accordingly, the tab 522 and the one or more openings 524 facilitate the securement of the second body portion 514 to the anvil assembly 550. As such, the first body portion 112 is secured to the cartridge housing 64 (e.g., via catch 68, adhesive, and/or any other suitable chemical or mechanical connection) and the second body portion 514 is secured to the anvil assembly 550 via the one or more attaching features 520 and the one or more openings 524.

Referring now to FIGS. 21-24, one embodiment of an end effector 640 having another embodiment of a surgical buttress 610 positioned thereon or operatively associated therewith is illustrated. End effector 640 is substantially similar to end effector 40 and will be described in detail herein to the extent necessary to describe the differences in construction and operation thereof. End effector 640 includes an anvil assembly 650 that includes one or more channels 652 extending longitudinally along side edges thereof and projecting form a tissue contacting surface thereof. The one or more channels 652 are configured and dimensioned to receive the surgical buttress 610 such that at least a portion of the surgical buttress 610 is positioned within the one or more channels 652. The one or more channels 652 may extend at least a portion of the length of anvil assembly 650 (see FIGS. 23-24).

The surgical buttress 610 includes a first body portion 112, similar to surgical buttress 110, and a second body portion 614. The second body portion 614 is positionable within the one or more channels 652 so that the second body portion 614 is held or maintained against the tissue contacting surface of the anvil assembly 650. In particular, the second body portion 614 includes one or more attaching features 620 defined by the peripheral side edges 620a, 620b thereof. The peripheral side edges 620a, 620b of second body portion 614 are configured and dimensioned to be received within at least a portion of the channels 652. In this respect, the first body portion 112 may be secured to the cartridge housing 64 (e.g., via catch 68, adhesive, or any other suitable chemical or mechanical connection) and the peripheral side edges 620a, 620b of the second body portion 614 is secured to the anvil assembly 650 via the one or more channels 652.

Figure 25:
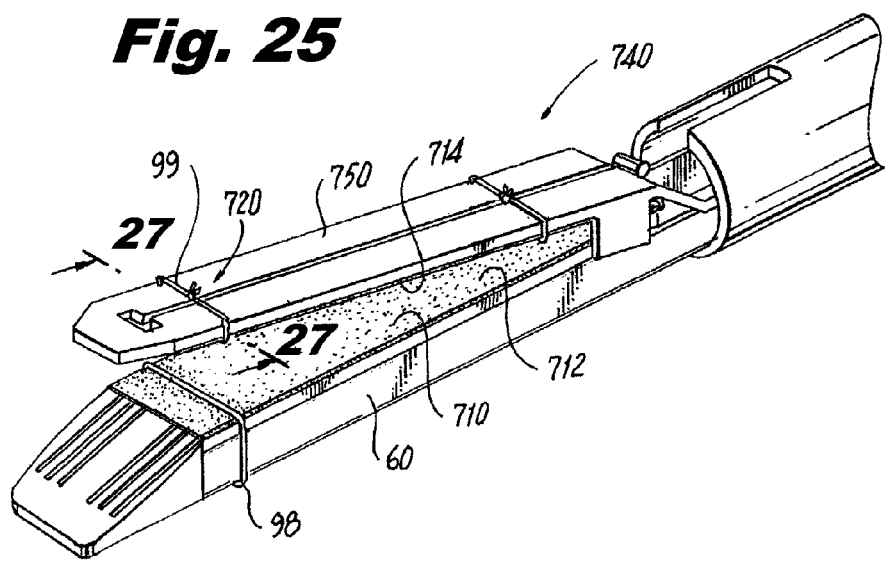
FIG. 25 is a perspective view of still another embodiment of an end effector having another embodiment of a surgical buttress positioned thereon in accordance with the present disclosure.
Figure 26:
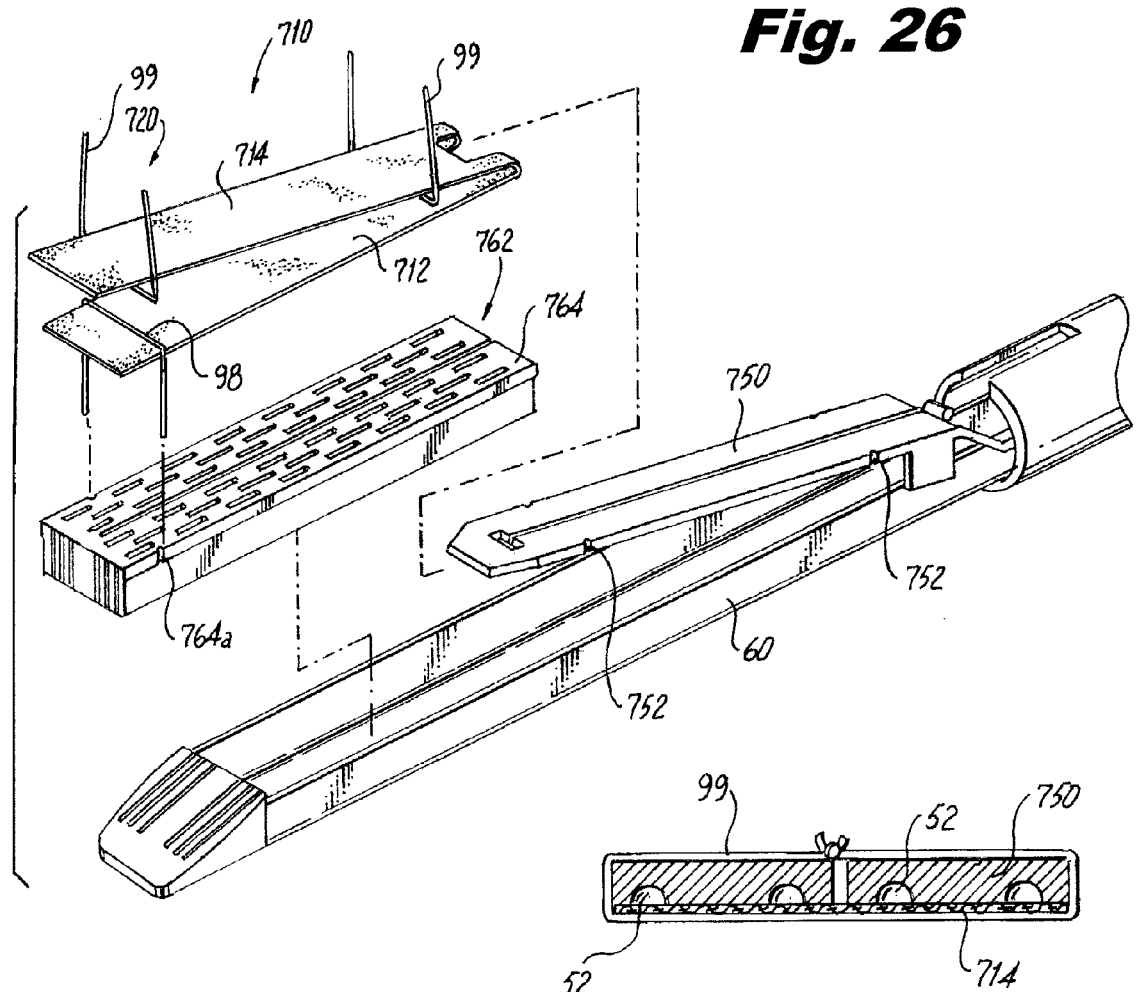
FIG. 26 is an exploded perspective view of the end effector shown in FIG. 25.
Figure 27:
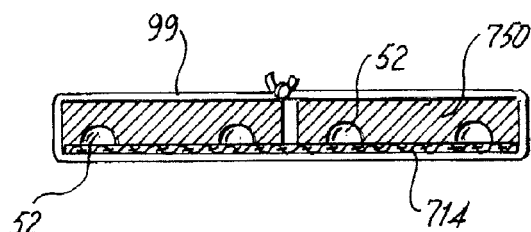
FIG. 27 is a cross-sectional view of the indicated area of detail of FIG. 26.

Referring now to FIGS. 25-27, one embodiment of an end effector 740 having another embodiment of a surgical buttress 710 positioned thereon or operatively associated therewith is illustrated. End effector 740 is substantially similar to end effector 40 and will be described herein to the extent necessary to describe the differences in construction and operability thereof. End effector 740 includes an anvil assembly 750 that defines one or more indentations or notches 752 formed in opposed side edges thereof. The one or more notches 752 are configured and dimensioned to receive a suture 99 therein. The surgical buttress 710 includes a first body portion 712, similar to surgical buttress 110, and a second body portion 714.

Surgical buttress 710 includes one or more attaching features 720 in the form of sutures 98, 99 disposed in mechanical cooperation with each of the first and second body portions 712, 714, respectively. The sutures 98, 99 may be separately coupled to one or both of the first and second body portions 712, 714 while securing the surgical buttress 710 to the end effector 740. Suture 98 facilitates the securement of the first body portion 712 to a cartridge housing 764 of a staple cartridge 762.

The cartridge housing 764 defines indentations or notches 764a in side edges thereof such that the suture 98 may be threaded through the notches 764a and tied together for securing the first body portion 712 to the cartridge housing 764 of the staple cartridge 762. Similarly, sutures 99 facilitate the securement of the second body portion 714 to the anvil assembly 750 such that sutures 99 may be threaded through the notches 752 and tied together. In this respect, the first body portion 712 is secured to the cartridge housing 764 and/or the first jaw 60 while the second body portion 714 is secured to the anvil assembly 750 when each of the first and second body portions 712, 714 are secured to the end effector 740 via sutures 98, 99. Either the first body portion 712 and/or the second body portion 714 may be secured to the end effector 740 via adhesive, snap-fit, and/or any other suitable chemical or mechanical connection.

In general, linear staplers, including open and endoscopic devices, can have two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such an instrument is disclosed, for example, in U.S. Pat. No. 6,202,914, the entire content of which is incorporated herein by reference.

Some staplers apply a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. An example of such a stapler is disclosed in U.S. Pat. No. 5,065,929, the entire content of which is incorporated herein by reference.

Some of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,865,361, the entire content of which is incorporated herein by reference.

It is further contemplated that the surgical buttress may be configured for use with a circular stapling apparatus, or a semi-circular stapling apparatus. Surgical stapling devices for applying an annular array of staples or fasteners to tissue are well known in the art. These devices typically include means for controlling the spacing between the fastener assembly and the anvil member at the distal end of the apparatus. The fastener assembly generally includes a circular array of fasteners such as staples, anastomosis rings, and the like, while the anvil member includes means for completing the circular anastomosis, typically an array of bucket members that clinch the staples after the staples are expelled from the fastener assembly, or may include a locking member for the anastomosis ring. The means for advancing or retracting the anvil in relation to the fastener assembly typically includes a wing-nut type mechanism at a proximal end of the instrument or a rotatable knob member, both of which engage a worm gear arrangement in the handle mechanism to slowly, and methodically advance the anvil member towards the fastener assembly.

Surgical stapling devices for applying an annular array of staples, as well as devices for completing a surgical anastomosis through the provision of anastomosis rings, are well known in gastric and esophageal surgery, for example in classic or modified gastric reconstruction typically formed in an end to end, end to side, or side to side manner. In use, the instrument is positioned within the lumen of an organ such as the stomach, esophagus, or intestine in order to perform the anastomosis. The tissue is positioned between the anvil and the fastener assembly and is typically tied off, for example, by a purse string suture. Thereafter, the anvil member is advanced towards the fastener assembly by rotation of the rotatable knob or wing nut assembly at the proximal end of the instrument to hold the tissue between the anvil member and the fastener assembly. As the staples or the fasteners are expelled from the fastener assembly, a circular knife typically follows the application of the staples to excise unwanted tissue at the anastomosis site. The instrument is then removed from the lumen of the organ.

Closing mechanisms associated with these types of stapling or fastening devices typically utilize a complex worm gear arrangement or screw bearing member to open and close the spacing between the anvil and the fastener assembly. These devices generally provide a rotatable knob or wing-like assembly remote from the fastener or staple pusher member, and the worm gear mechanism is provided to translate the rotational movement of the knob into longitudinal movement of the anvil member towards the staple pusher member. In order to effect this movement, the surgeon must grasp the device with one hand while rotating the knob or wing-like assembly with the other hand. Such instruments are disclosed, for example, in U.S. Pat. No. 5,915,616, the entire content of which is incorporated herein by reference.

In embodiments, the surgical buttress is configured for use with surgical fastening devices for simultaneously applying an array of surgical fasteners, e.g., staples or other types of fasteners that are known in the art. Such devices are used for joining body tissue such as, for example, intestinal and gastric walls with spaced parallel rows of longitudinally aligned fasteners. These surgical fastening devices reduce the time of wound closure in a surgical procedure.

Typically, these devices include a fastener holder disposed on one side of the tissue to be joined, and an anvil assembly parallel to the fastener holder on the other side of the tissue to be fastened. The fastener holder is moved linearly towards the anvil assembly so that the tissue is clamped between them. The fasteners are driven from the fastener holder so that the ends of the fasteners pass through the tissue and form finished fasteners as they make contact with the anvil assembly, thereby producing an array of finished fasteners in the tissue. The fasteners can be one or two piece and made of metal, non-absorbable polymers, or bioabsorbable polymers such as polyglycolide, polylactide, and copolymers thereof.

U.S. Pat. No. 5,137,198 to Nobis et al. ("Nobis") discloses a fastener applying device including a cartridge that is advanced towards an anvil assembly by an advancing mechanism. The advancing mechanism includes a first actuator member for advancing the cartridge towards the anvil assembly at an accelerated rate and a second actuator member spaced from the first actuator member for incrementally advancing the cartridge towards the anvil assembly.

Typically, these fastener applying devices include a pusher bar that is advanced over a predetermined stroke to interact with and eject the fasteners from the cartridge. At least one driver is positioned within the cartridge between the distal end of the pusher bar and the fasteners such that the pusher bar advances the drivers into engagement with the fasteners. The length of the drivers may be varied to facilitate ejection of different size fasteners from a fastener applying device having a fixed pusher bar stroke. Such instruments are disclosed, for example, in U.S. Pat. No. 5,964,394, the entire content of which is incorporated herein by reference.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Thus the scope of the embodiments should be determined by the appended claims and their legal equivalents, rather than by the examples given.

What is claimed is:

1. A surgical staple cartridge assembly for selective use with a surgical stapling apparatus having a first jaw in the form of an anvil assembly and a second jaw configured to selectively receive a staple cartridge assembly, the staple cartridge assembly comprising:
   a cartridge housing defining a longitudinal axis, the cartridge housing including a tissue contacting surface having a plurality of rows of staple retaining slots formed therein, wherein the cartridge housing defines a knife slot;
   a staple disposed in each staple retaining slot; and
   a surgical buttress having a first body portion secured to and overlying the tissue contacting surface of the cartridge housing so that a longitudinal axis of the first body portion of the surgical buttress is substantially aligned with the longitudinal axis of the cartridge housing, the surgical buttress further including a second body portion extending distally from a proximal portion of the first body portion so that the second body portion extends at least partially over the first body portion;
   wherein the proximal portion of the first body portion and a proximal portion of the second body portion of the surgical buttress each include a notch formed therein, each notch being axially aligned with the knife slot.

2. The surgical staple cartridge assembly according to claim 1, wherein a distal end of the first body portion of the surgical buttress extends distally of a distal-most staple retaining slot of the cartridge housing, and the proximal portion of the first body portion of the surgical buttress extends proximally of the staple retaining slots of the cartridge housing.

3. The surgical staple cartridge assembly according to claim 1, wherein the second body portion of the surgical buttress includes at least one attaching feature configured to selectively attach the second body portion to the anvil assembly when the surgical staple cartridge assembly is connected to the second jaw.

4. The surgical staple cartridge assembly according to claim 3, wherein the at least one attaching feature includes a strap extending transversely across the second body portion.

5. The surgical staple cartridge assembly according to claim 4, wherein the strap is disposed on a side of the second body portion facing a tissue contacting surface of the anvil assembly when the surgical staple cartridge assembly is connected to the second jaw.

6. The surgical staple cartridge assembly according to claim 3, wherein the at least one attaching feature includes a tab extending from a distal end of the second body portion, where the tab defines an aperture therein that is configured and dimensioned to receive a portion of the anvil assembly.

7. The surgical staple cartridge assembly according to claim 1, wherein the surgical buttress is biodegradable.

8. The surgical staple cartridge assembly according to claim 1, wherein the surgical buttress is non-biodegradable.

9. A surgical staple cartridge for selective use in a stapling apparatus having a first jaw in the form of an anvil assembly and a second jaw configured to selectively receive the staple cartridge, the staple cartridge comprising:
   a cartridge housing;
   a plurality of staples disposed in staple slots formed in the cartridge housing; and
   a surgical buttress having first and second body portions, the first body portion being mounted to the cartridge housing and the second body portion being configured and dimensioned to be removably coupled to the anvil assembly when the staple cartridge is operably coupled with the second jaw, wherein the second body portion is configured and dimensioned to substantially overlie at least some fastener pockets defined in the anvil assembly, and wherein the first body portion substantially overlies at least some of the staple slots of the cartridge housing;
   wherein at least one of the first and second body portions define a passage that permits longitudinal passage of a knife of the surgical stapling apparatus therethrough, the knife extending above a tissue contacting surface of the cartridge housing.

10. The surgical staple cartridge according to claim 9, wherein the second body portion includes at least one attaching feature that is configured and dimensioned to removably operably couple the second body portion to the anvil assembly.

11. The surgical staple cartridge according to claim 10, wherein the at least one attaching feature includes at least one band configured and dimensioned to extend across a back of the anvil assembly.

12. The surgical staple cartridge according to claim 10, wherein the at least one attaching feature includes a tab extending from the second body portion, wherein the tab defines an aperture therein.

13. The surgical staple cartridge according to claim 9, wherein the staple cartridge is disposable.

14. The surgical staple cartridge according to claim 9, wherein at least a portion of the first and second body portions of the at least one surgical buttress is made from biodegradable materials selected from the group consisting of: natural collagenous materials, cat gut, and synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof.

15. A surgical stapling apparatus according to claim 9, wherein at least a portion of the first and second body portions of the at least one surgical buttress is made from non-biodegradable materials selected from the group consisting, of: polyolefins, polyethylene, polydimethylsiloxane, polypropylene, copolymers of polyethylene and polypropylene, blends of polyethylene and polypropylene, ultra high molecular weight polyethylene, polyamides, polyesters, polyethylene terephthalate, polytetrafluoroethylene, polyether-esters, polybutester, polytetramethylene ether glycol, 1,4-butanediol, and polyurethanes.

* * * * *